United States Patent
Mouchawar et al.

(10) Patent No.: US 7,065,403 B1
(45) Date of Patent: Jun. 20, 2006

(54) SYSTEM AND METHOD FOR MEASURING LEAD IMPEDANCE IN AN IMPLANTABLE STIMULATION DEVICE EMPLOYING PULSE-TRAIN WAVEFORMS

(75) Inventors: Gabriel A. Mouchawar, Valencia, CA (US); Jorge N. Amely-Velez, Simi Valley, CA (US); Steven W. Badelt, Granada Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 603 days.

(21) Appl. No.: 10/306,502

(22) Filed: Nov. 26, 2002

Related U.S. Application Data

(60) Provisional application No. 60/337,410, filed on Dec. 3, 2001.

(51) Int. Cl.
*A61N 1/36* (2006.01)
(52) U.S. Cl. .................. 607/8; 607/28; 607/74
(58) Field of Classification Search .......... 607/8, 607/28, 68, 70, 72, 74
See application file for complete search history.

(56) References Cited

U.S. PATENT DOCUMENTS

| | | | | |
|---|---|---|---|---|
| 5,271,395 | A | 12/1993 | Wahlstrand et al. | 607/9 |
| 5,453,698 | A | 9/1995 | Williams et al. | 324/678 |
| 5,549,646 | A | 8/1996 | Katz et al. | 607/8 |
| 5,713,935 | A * | 2/1998 | Prutchi et al. | 607/28 |
| 5,722,997 | A * | 3/1998 | Nedungadi et al. | 607/28 |
| 5,755,742 | A | 5/1998 | Schuelke et al. | 607/27 |
| 5,782,884 | A | 7/1998 | Stotts et al. | 607/17 |
| 5,824,029 | A * | 10/1998 | Weijand et al. | 607/122 |
| 5,897,577 | A | 4/1999 | Cinbis et al. | 607/28 |
| 5,974,339 | A | 10/1999 | Baker, Jr. et al. | 607/7 |
| 5,999,854 | A | 12/1999 | Deno et al. | 607/18 |
| 6,104,954 | A * | 8/2000 | Blunsden | 607/8 |
| 6,317,633 | B1 | 11/2001 | Jorgenson et al. | 607/28 |
| 6,406,421 | B1 | 6/2002 | Grandjean et al. | 600/17 |
| 6,445,951 | B1 * | 9/2002 | Mouchawar | 607/28 |
| 6,595,927 | B1 * | 7/2003 | Pitts-Crick et al. | 600/529 |

FOREIGN PATENT DOCUMENTS

| | | |
|---|---|---|
| EP | 0715866 A2 | 6/1996 |
| EP | 0715866 A3 | 7/1998 |
| WO | WO 98/19738 | 5/1998 |
| WO | WO 99/24113 | 5/1999 |
| WO | WO 02/18009 A1 | 3/2002 |

* cited by examiner

*Primary Examiner*—Carl Layno

(57) ABSTRACT

A leakage detection system for use in an implantable cardiac stimulation device, such as a cardioverter defibrillator. The leakage detection system includes a switch bank and a controller that regulates the switching arrangements of various switches. The leakage detection system causes pulse generators to generate a pulse-train waveform comprised of a sequence of pulses of opposite polarities, and to deliver these pulses in a preselected temporal relation. The controller detects the current leakage from the pulse generator to the tissues by sensing and analyzing the voltage or current of the pulse generator, leads, and electrodes. The pulsatility and alternating polarities of biphasic pulse-train waveforms increase the stimulation threshold of the motor or sensory nerves and excitable tissues.

25 Claims, 5 Drawing Sheets

SYSTEM AND METHOD FOR MEASURING LEAD IMPEDANCE IN AN IMPLANTABLE STIMULATION DEVICE EMPLOYING PULSE-TRAIN WAVEFORMS

PRIORITY CLAIM

This application claims the priority of copending U.S. provisional patent application, titled "System and Method for Imperceptible Lead Integrity Checking in an Implantable Stimulation Device," Ser. No. 60/337,410, filed on Dec. 3, 2001, which is assigned to the same assignee as the present invention and which is incorporated herein by reference in its entirety.

FIELD OF THE INVENTION

The present invention generally relates to implantable cardiac stimulation devices. More specifically, this invention relates to an implantable cardioverter defibrillator and associated method for measuring the patient impedance. The impedance measuring system employs pulse-train waveforms for checking the integrity of various leads implanted in a patient's dysfunctional heart.

BACKGROUND OF THE INVENTION

In the normal human heart, the sinus node, that is generally located near the junction of the superior vena cava and the right atrium, constitutes the primary natural pacemaker initiating rhythmic electrical excitation of the heart chambers. Disruption of the heart's natural pacemaker and conduction system, as a result of aging and/or disease, can be successfully treated using various implantable cardiac stimulation devices, including pacemakers and implantable cardioverter defibrillators. A pacemaker is generally arranged to deliver rhythmic electrical pulses to the heart to maintain a normal rhythm in patients having bradycardia, which is too slow of heart rate, or other conduction abnormalities. In contrast, an implantable cardioverter defibrillator, commonly referred to as an "ICD", can recognize tachycardia and/or fibrillation and deliver electrical therapy in order to terminate such arrhythmias. In addition, such ICDs may often be configured to perform pacemaking functions (or pacing) as well.

Depending upon the patients' needs, the ICDs generate pacing, cardioverting, and/or defibrillating pulses, and deliver them to excitable cardiac tissues of the patients' heart by means of implanted electrical leads and electrodes. Since the lead is an essential part of the therapy a lead failure renders the device ineffective.

To detect lead failure, the cardiac stimulation devices, such as ICDs, monitor the impedance of the implanted leads. For high-voltage leads, a sudden rise of the lead impedance above 100 ohms is generally considered a signs of lead failure. To this end, certain conventional stimulation devices incorporate a high-voltage lead integrity check (HVLIC) system that generates a detection waveform, delivers the waveform through the implanted leads, and checks the integrity of the leads based on the delivered waveform parameters measured by the device.

In a conventional method of performing high-voltage lead integrity check a 12V, 3 msec truncated exponential pulse illustrated in FIG. 3, is delivered from the high voltage capacitors through the defibrillation leads. The low amplitude of this pulse is an attempt to get below perception thresholds of sensory and motor nerves and muscle tissue. The 3 msec duration of this pulse is chosen to allow enough time to enable the measurement of a voltage change across the high voltage capacitors of the implantable device. Several problems are associated with the monophasic detection waveform of FIG. 3. First, the duration of 3 msec is generally much longer than the time constants of the sensory and/or motor nerves that are generally on the order of 200 μsec to 500 μsec. In fact, such a duration almost approaches the time constant for stimulation of de-innervated muscles, and could thus cause muscle twitches and sensation.

In addition, the ICD is designed to charge its high voltage capacitors to about 800 volts with 2% accuracy. However, this accuracy degrades when charging to, or measuring lower voltages. This loss of accuracy is compounded by measurement errors associated with even lower voltages, and results in an inaccurate high-voltage lead integrity check of the lead impedance.

Another problem is that approximately 3 volts of the monophasic detection waveform is consumed in polarizing of the electrode-electrolyte interface at the electrodes and body fluids boundary. This voltage drop occurs, for example, between the blood and a polished platinum electrode, obscuring the delivered signal and compounding the inaccuracy of the measurement of the lead impedances.

Accordingly, it would be desirable to provide a more reliable impedance measurement system for the cardiac stimulation device, which need has heretofore remained unsatisfied.

SUMMARY

The present invention addresses the above needs by providing an implantable stimulation device, such as a cardioverter defibrillator (ICD), which is equipped with a lead impedance measuring circuit that employs pulse-train waveforms to check the integrity of various leads implanted in a patient's dysfunctional heart.

A feature of this invention is to provide a cardiac stimulation device that comprises at least one pulse generator for generating electrical pulses; a plurality of electrodes that are positioned in electrical contact with excitable cardiac tissues; and a plurality of leads that deliver the electrical pulses from the pulse generator to the cardiac tissues.

An impedance measurement system generally comprises at least one switch bank and a controller. The switch bank comprises of multiple switches that connects the pulse generator to the leads to permit multiple switching arrangements. The controller actuates the switches of the switch bank to select an optimal switching arrangement, to generate a waveform composed of a first set of pulses with a first polarity, and a second set of pulses with a second polarity that is opposite to the first polarity. With such a switching arrangement, the first and second pulses are delivered in a pre-selected temporal relation, the ICD measures the voltage before and after the delivery of the pulse and calculates the resulting tissue impedance across the leads.

The switch bank comprises an H-bridge that includes at least two of switches along each leg of the H-bridge. The use of such an H-bridge is known in the field.

The waveform comprises first and second pulses that are delivered in an alternating order. The first and second set of pulses have alternating polarity. Each of these pulses has a duration less than about 15% or 10% of a time constant of stimulation of the tissues. Preferably, each pulse has a duration of less than 50 μsec. At least one of the first and second pulses may have a voltage higher than 12 volts, wherein the voltages of each pulse decreases exponentially.

The waveform is comprised of a train of pulses. The train is comprised of more than 10 pulses (or pairs of pulses of different polarities).

The temporal relation of the pulses that are delivered by the selected switching arrangement preferably relate to a cardiac event.

The pulse generator may generate multiple waveforms for delivery via the leads, each waveform including an initial pulse and a terminal (or last) pulse. These waveforms can be identical or similar, and they can be separated by a preselected period of time. As stated earlier, the voltages of the pulses within each waveform decrease exponentially. In the event of a sequence of waveforms, the terminal pulse voltage of the preceding waveform is substantially equal to the initial pulse voltage of the succeeding waveform.

The impedance measuring system includes a method to measure the leading and trailing waveform voltage in the pulse generator. The pulse generator or the external programmer can analyze the measured leading and trailing voltages and calculate the patient's lead impedance. Starting with the equation for exponential decay:

$$Vtrailing = Vleading \cdot e^{\frac{-d}{R \cdot C}}$$

where, $V_{trailing}$ is the waveform's trailing voltage, $V_{leading}$ is the initial waveform voltage, d is the effective duration (on time of the switches), C is the generator capacitance and R is the patient impedance, the patient impedance R can be solved using the following relationship between the patient impedance and the other waveform parameters:

$$R = \frac{d}{\left(\ln\left(\frac{Vleading}{Vtrailing}\right) \cdot C\right)}$$

This impedance measuring system offers various benefits by using pulse-train detection waveforms. For example, the pulsatility and alternating polarities of the biphasic pulse-train waveform will result in a higher stimulation threshold of the motor or sensory nerves and excitable tissues. This results in reducing the patient's sensation associated with the delivery of a conventional waveform. In addition, this impedance measuring system can employ pulse-train waveforms with higher amplitudes to improve accuracy of measurement of the patient lead impedance.

Moreover, this system can deliver a pulse-train waveform for a prolonged duration so that the trailing pulse of the waveform has a smaller amplitude than the leading pulse, thereby generating a greater voltage drop between the leading and trailing pulses. A larger drop improved the signal to noise ratio of the measurement further improving its accuracy.

Furthermore, the alternating biphasic feature of the pulse-train waveform as well the shorter duration of each pulse (i.e., higher frequency) avoid or at least minimize polarization voltage across the electrode electrolyte interface (i.e., the interface between the electrode surfaces and the body fluids). Polarization voltage subtracts from the voltage delivered to the patient. This loss of signal represent another source of inaccuracy. By reducing the polarization loss further improves the accuracy of the measured impedance.

BRIEF DESCRIPTION OF THE DRAWINGS

Various features of the present invention and the manner of attaining such will now be described in greater detail with reference to the following description, claims, and drawings, wherein reference numerals are reused when appropriate, to indicate a correspondence between the referenced items, and wherein:

DETAILED DESCRIPTION OF PREFERRED EMBODIMENTS

The following description is of a best mode presently contemplated for practicing the present invention. This description is not to be taken in a limiting sense but is made merely for the purpose of describing the general principles of the invention. The present invention is directed at an improved patient impedance measuring system for implantable cardiac stimulating devices with pacemaking, cardioversion, and/or defibrillation capabilities.

Figure 1:
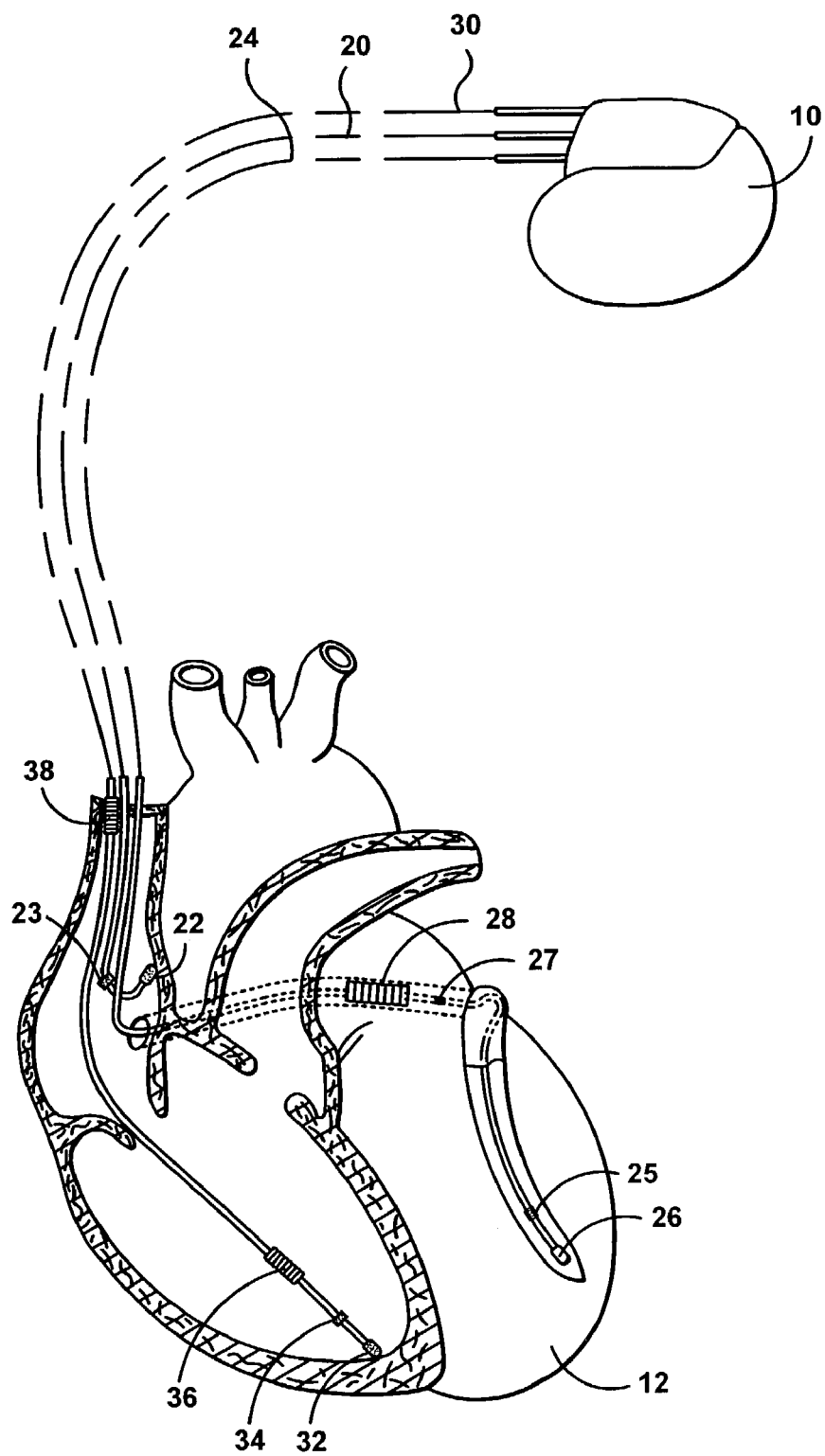
FIG. 1 is a simplified, partly cut-away view of an exemplary implantable cardiac stimulation device in electrical communication with at least three leads implanted into a patient's heart for delivering multi-chamber stimulation and shock therapy according to the present invention.
Figure 2:
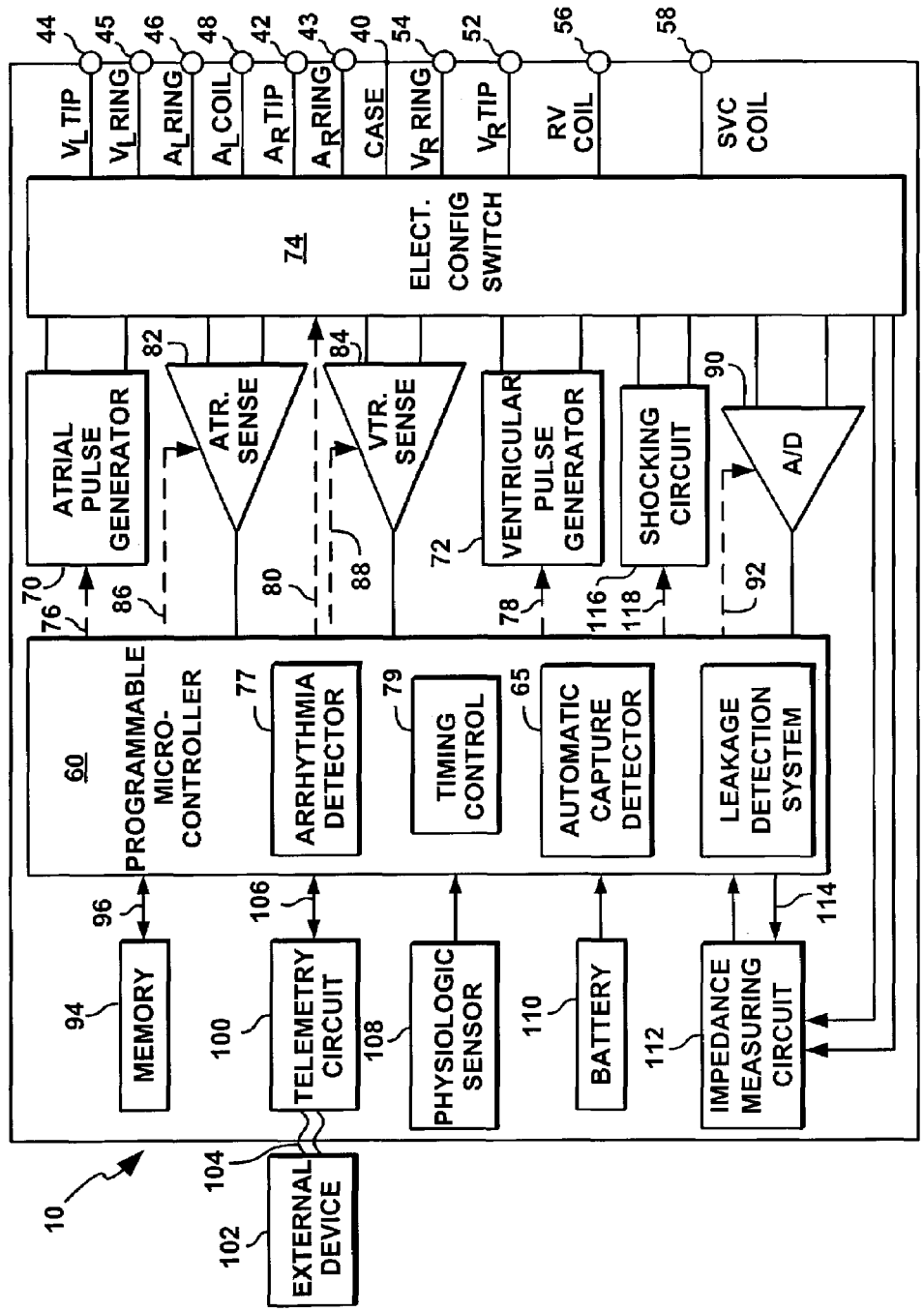
FIG. 2 is a functional block diagram of the exemplary implantable cardiac stimulation device of FIG. 1, illustrating the basic elements providing pacing stimulation, cardioversion, and defibrillation in four chambers of the heart, and incorporating a patient lead impedance measuring circuit of the present invention.
Figure 3:
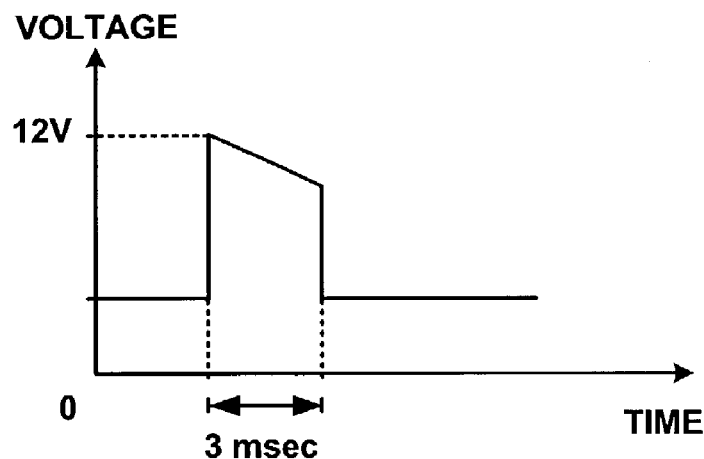
FIG. 3 illustrates a prior art monophasic waveform used to measure a patient lead impedance.

A cardiac stimulation device will thus be described in conjunction with FIGS. 1 and 2, in which the features included in this invention could be implemented. It is recognized, however, that numerous variations of such a device exist in which various methods included in the present invention can be implemented without deviating from the scope of the present invention.

FIG. 1 illustrates a stimulation device 10 in electrical communication with a patient's heart 12 by way of three leads 20, 24 and 30 suitable for delivering multi-chamber stimulation and/or shock therapy. To sense atrial cardiac signals and to provide right atrial chamber stimulation therapy, the device 10 is coupled to an implantable right atrial lead 20 including at least one atrial tip electrode 22 that typically is implanted in the patient's right atrial appendage. The right atrial lead 20 may also include an atrial ring electrode 23 to allow bipolar stimulation or sensing in combination with the atrial tip electrode 22.

To sense the left atrial and left ventricular cardiac signals and to provide left-chamber stimulation therapy, the stimulation device 10 is coupled to a "coronary sinus" lead 24 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and/or ventricular cardiac signals; deliver left ventricular pacing therapy using at least one left ventricular tip electrode 26 for unipolar configurations or in combination with left ventricular ring electrode 25 for bipolar configurations; deliver left atrial pacing therapy using at least one left atrial ring electrode 27 as well as shocking therapy using at least one left atrial coil electrode 28.

The stimulation device 10 is also shown in electrical communication with the patient's heart 12 by way of an implantable right ventricular lead 30 including, in this embodiment, a right ventricular (RV) tip electrode 32, a right ventricular ring electrode 34, a right ventricular coil electrode 36, a superior vena cava (SVC) coil electrode 38, and so on. Typically, the right ventricular lead 30 is inserted transvenously into the heart 12 so as to place the right ventricular tip electrode 32 in the right ventricular apex such that the RV coil electrode 36 is positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

FIG. 2 illustrates a simplified block diagram of the multi-chamber implantable stimulation device 10, which is capable of treating both fast arrhythmia and slow arrhythmia with stimulation therapy, including cardioversion, defibrillation, and pacing stimulation. While a particular multi-chamber device is shown, this is for illustration purposes only, and one of ordinary skill in the pertinent art could readily duplicate, eliminate or disable the appropriate circuitry in any desired combination to provide a device capable of treating the appropriate chamber(s) with cardioversion, defibrillation, and/or pacing stimulation.

The stimulation device 10 includes a housing 40 which is often referred to as "can", "case," or "case electrode," and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 further includes a connector having a plurality of terminals 42, 43, 44, 45, 46, 48, 52, 54, 56, and 58 (shown schematically and, for convenience, the names of the electrodes to which they are connected are shown next to corresponding terminals). As such, in order to achieve right atrial sensing and stimulation, the connector includes at least one right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and/or shocking, such a connector includes a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, that are adapted for connection to the left ventricular tip electrode 26, the left ventricular ring electrode 25, the left atrial ring electrode 27, and the left atrial coil electrode 28, respectively.

To support right ventricular sensing, pacing, and/or shocking, the connector may further include a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular (RV) tip electrode 32, the RV ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may include RAM or ROM memory, logic and timing circuitry, state machine circuitry, and/or I/O circuitry. Typically, the microcontroller 60 may have the ability to process or monitor various input signals (data) as controlled by a program code stored in a designated block of memory.

FIG. 2 illustrates an atrial pulse generator 70 and ventricular pulse generator 72 which generate stimulation pulses for delivery by the right atrial lead 20, the right ventricular lead 30, and/or the coronary sinus lead 24 via a switch 74. It is understood that, to provide the stimulation therapy in each of the four chambers of the heart, the atrial pulse generator 70 and the ventricular pulse generator 72 may include, e.g., dedicated pulse generators, independent pulse generators, multiplexed pulse generators, and/or shared pulse generators. The atrial pulse generator 70 and the ventricular pulse generator 72 are generally controlled by the microcontroller 60 via appropriate control signals 76 and 78, respectively, to trigger or inhibit the stimulation pulses.

The microcontroller 60 may further include timing control circuitry 79 which may be used to control timing of the stimulation pulses such as, e.g., pacing rate, atrio-ventricular (AV) delay, atrial interchamber (A-A) delay, and/or ventricular interchamber (V-V) delay. Such timing control circuitry 79 may also be used to keep track of the timing of refractory periods, noise detection windows, evoked response windows, alert intervals, marker channel timing, and so on.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, and the like) by selectively closing the appropriate combination of switches. Atrial sensing circuits 82 and ventricular sensing circuits 84 may also be selectively coupled to the right atrial lead 20, coronary sinus lead 24, and the right ventricular lead 30 through the switch 74, for detecting the presence of cardiac activity in each of the four chambers of the heart.

Accordingly, the atrial sensing circuit 82 and the ventricular sensing circuit 84 may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each of the atrial and ventricular sensing circuits 82, 84 preferably employs one or more low power, precision amplifiers with programmable gain, automatic gain or sensitivity control, band-pass filtering, and threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial sensing circuit 82 and ventricular sensing circuits 84 may be connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, may receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm may be physiologic or pathologic. As used herein, "sensing" generally refers to the process of noting an electrical signal, while "detection" generally refers to the step of confirming the sensed electrical signal as the signal being sought by the detector. As an example, "detection" applies to the detection of both proper rhythms (i.e., "P wave" or "R wave") as well as improper disrhythmias including arrhythmia and bradycardia (e.g., detection of the absence of a proper rhythm).

The timing intervals between sensed events (e.g., P-waves, R-waves, and depolarization signals associated with fibrillation which are sometimes referred to as "F-waves" or "Fib-waves") are then classified by the arrhythmia detector 77 by comparing them to a predefined rate zone limit (e.g., bradycardia, normal, low rate ventricular tachycardia, high rate ventricular tachycardia, fibrillation rate zones, and so on) and various other characteristics (e.g., sudden onset, stability, physiologic sensors, morphology, and so on), in order to determine the type of remedial therapy required (e.g., bradycardia pacing, anti-tachycardia stimulation, cardioversion shocks or defibrillation shocks, collectively referred to as "tiered therapy").

Cardiac signals are also applied to the inputs of a data acquisition system 90 which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. Such a data acquisition system 90 may be coupled to the right atrial lead 20, the coronary sinus lead 24, and the right ventricular lead 30 through the switch 74 to sample the cardiac signals across any pair of desired electrodes.

Advantageously, such a data acquisition system 90 may be coupled to the microcontroller 60 and/or another detection circuitry, for detecting an evoked response from the heart 12 in response to an applied stimulus, thereby aiding in the detection of "capture." In the embodiment of FIG. 2, the microcontroller 60 may include an automatic capture detector 65 which searches for an evoked response signal following a stimulation pulse during a "detection window" set by timing control circuitry 79. The microcontroller 60 enables the data acquisition system 90 via control signal 92 to sample the cardiac signal which falls in the capture detection window. The sampled signal is evaluated by the automatic capture detector 65 to determine if it is an evoked response signal based on its amplitude, peak slope, morphology or another signal feature or combination of the features. Detecting the evoked response during the detection window may indicate that capture has occurred.

The microcontroller 60 may further be coupled to a memory 94 by a suitable data/address bus 96, wherein the programmable operating parameters used by the microcontroller 60 are stored and modified, as required, so as to customize the operation of the stimulation device 10 to suit the needs of particular patients. Such operating parameters may define, e.g., stimulation pulse amplitude, pulse duration, polarity of electrodes, rate, sensitivity, automatic features, arrhythmia detection criteria, and/or the amplitude, shape of waves, and/or vector of each stimulation pulse to be delivered to the patient's heart 12 within each respective tier of therapy.

The stimulation device 10 may additionally include a power source that may be illustrated as a battery 110 for providing operating power to all the circuits of FIG. 2. For the stimulation device 10 employing shocking therapy, the battery 110 must be capable of operating at low current drains for long periods of time, preferably less than 10 µA, and also be capable of providing high-current pulses when the patient requires a shock pulse, preferably in excess of 2 A, at voltages above 2V, for periods of 10 seconds or more.

The implantable cardiac stimulation device 10 is equipped with an impedance measuring circuit 112 for measuring impedance between the high-voltage (HV) leads 40, 56 and 58 of the stimulation device 10. The impedance measuring circuit 112 employs pulse-train waveforms to decrease the patient sensation associated with the delivery of the impedance measuring waveform. It could also be used with higher amplitudes and prolonged durations to increase accuracy of the impedance measurement.

Figure 6:
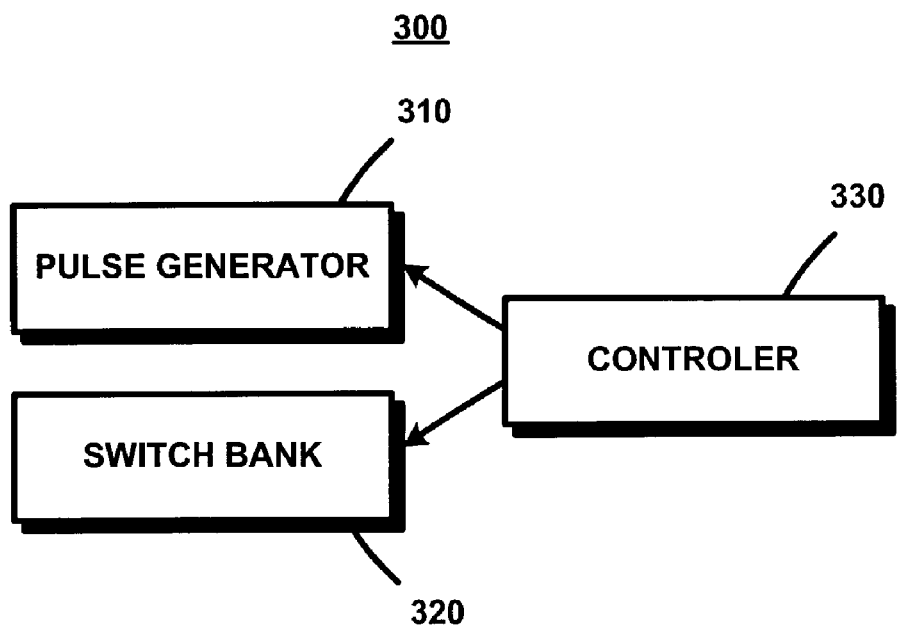
FIG. 6 is a high level block diagram of the lead impedance measuring circuit of the present invention.
Figure 4:
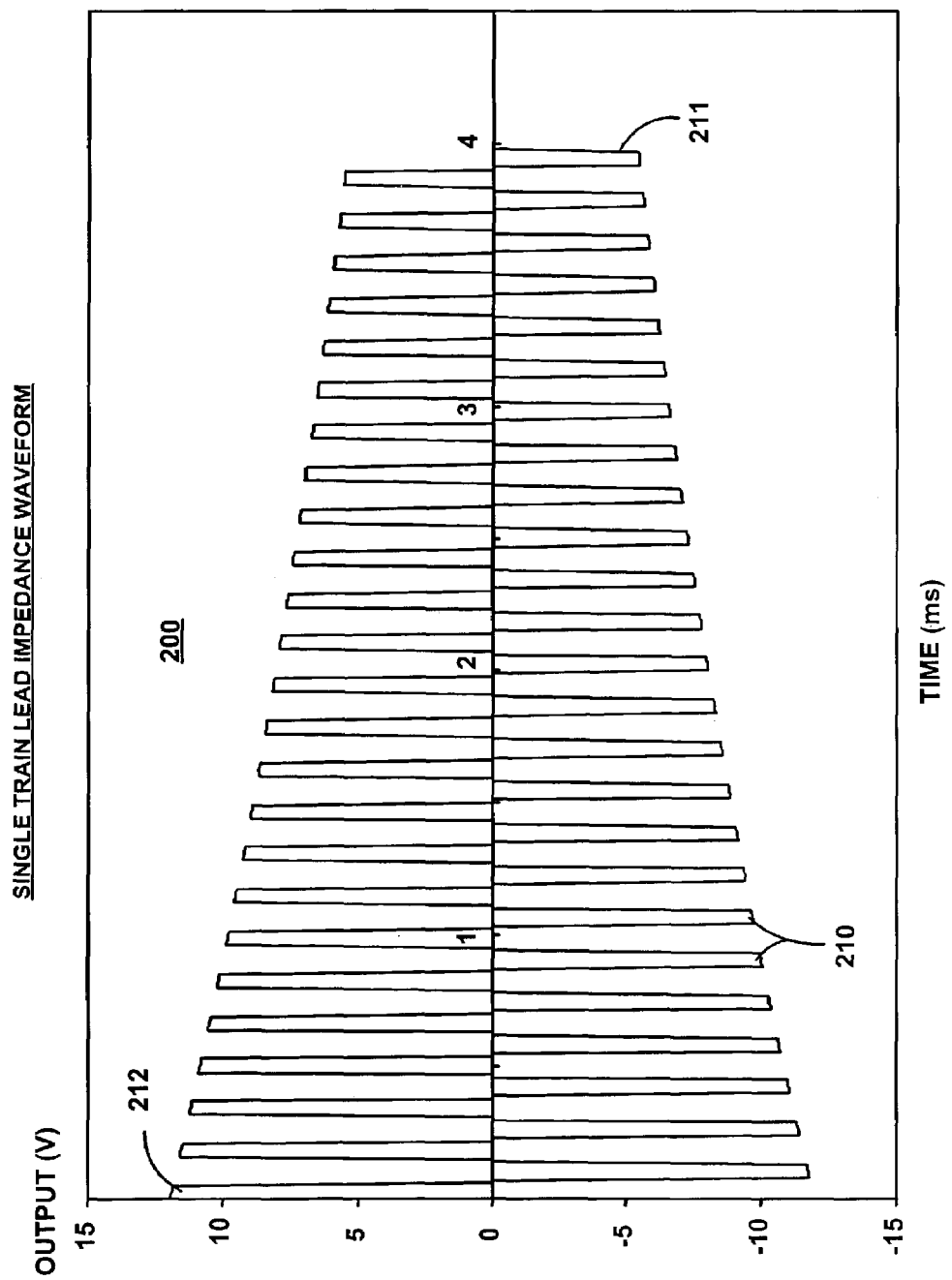
FIG. 4 is a graph of a biphasic pulse-train waveform used to measure the patient lead impedance according to the present invention.
Figure 5:
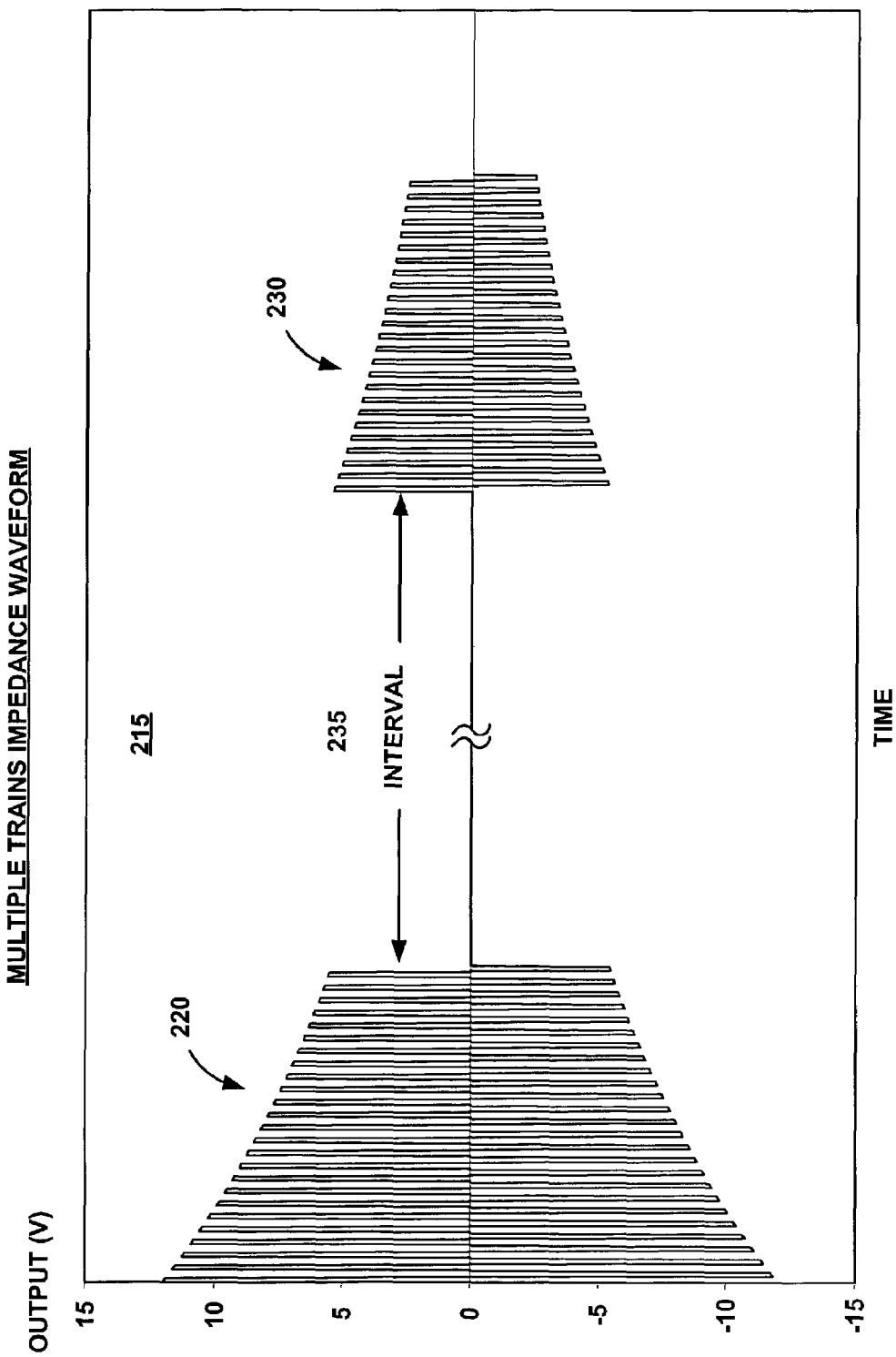
FIG. 5 is a graph of a sequence of biphasic pulse-train waveforms used by the impedance measuring circuit according to the present invention.

FIGS. 4 and 5 illustrate exemplary embodiments of pulse-train waveform used by the impedance measuring circuit 112 to achieve the objectives of the present invention. FIG. 6 illustrates the circuit used to generate the waveform of FIG. 4.

In one embodiment of the present invention, the impedance measuring circuit 112 generates a variety of biphasic pulse-train waveforms. As an example, FIG. 4 illustrates an exemplary biphasic pulse-train waveform 200 formed of a plurality of successive electrical pulses 210 with alternating polarities mode. In this example, the pulses 210 have substantially identical durations, with exponentially decreasing amplitudes.

The impedance measuring circuit 112 sets the duration of the pulses 210 to a minimal value so that the electrical stimulation of the nerves and cardiac tissues by the pulse-train waveform 200 may be prevented or at least minimized. In general, the time constant ($\tau_S$) of most motor and sensory nerves are in the range of approximately 200 µsec to 500 µsec, and those of the excitable cardiac tissues range from approximately 1000 µsec to 5000 µsec.

Accordingly, the impedance measuring system 112 sets the duration of each pulse 210 to only a fraction of the time constant ($\tau_S$) of most motor and sensory nerves, e.g., ranging from about 1% of $\tau_S$ to about 20% of $\tau_S$, or more particularly, about 10% of $\tau_S$ or about 50 µS. The total duration of the waveform 200 extends between approximately 1 and 10 milliseconds.

It is understood that the minimum durations of the pulses 210 achievable in a given stimulation device 10 are generally determined by the hardware characteristics of the stimulation device 10, such as the switching speed of the high voltage output stage devices and/or discharging dynamics of the capacitors. The temporal characteristics of the pulse-train measuring waveform 200 can avoid or minimize the twitches and/or patient sensation due to a reduction of the motor and sensory nerve stimulation.

The impedance measuring circuit 112 may also cause the voltage amplitudes of the pulses 210 of the pulse-train waveform 200 to exceed pre-selected levels. In general, errors in measuring impedance drastically increase as the charging and/or operating voltage levels decrease. As an example, the pulse generators 70, 72 of the stimulation device 10 are generally designed to charge up to 800 volts within a ±2% error range. However, such errors could increase to ±20% when the operating voltage falls to about 12 volts. The loss of accuracy may further be compounded by the errors in measuring the low voltage signals, resulting in inaccurate measurements of lead impedances.

Therefore, the impedance measuring circuit 112 is preferably arranged to maintain the amplitudes of the pulses 210 above 10 volts or, more particularly, above 5 volts but preferably below 50 volts.

The total duration of the pulse-train waveform 200 may be determined by a variety of factors. As an example, the impedance measuring circuit 112 may cause the generation of pulses 210 for a preset period so that the impedance measuring circuit 112 can generate pulse-train waveforms that include the same number of pulses as long as the pulse duration (or pulse frequency) is maintained at the same value (i.e., fixed or constant). In this example, the amplitudes of the initial and terminal pulses of the waveform 200 can be determined primarily by the charging status and/or the amount of energy stored in the pulse generators 70, 72, the switching device characteristics, the discharging capacitor characteristics, and the patient's lead impedance.

It should be clear that the fixed duration is not an essential requirement for the implementation of the present the invention, but is just a matter of design simplicity and mathematical convenience. As long the effective on-time of the waveform is known, the impedance can be calculated. This means that all variations are allowed in the pulse width and pulse spacing.

Accordingly, depending upon the charging status of the pulse generators 70, 72, the impedance measuring circuit 112 may generate pulse-train waveforms 200 with different shapes, even though their constituent pulses 210 have the same duration or frequency. Alternatively, the impedance measuring circuit 112 may terminate the generation of the pulses 210 when the voltage of the terminal pulse 211 of the waveform 200 reaches or falls below a preset percentage (or ratio) of the voltage of the initial pulse 212, when the voltage of the terminal pulse 211 reaches or falls below a preset threshold, or when the pulses 210 of the waveform 200 deliver a preset amount of electrical energy to the surrounding tissues. Although this embodiment does not require the pulse-train waveform 200 to have a preset duration, it may allow the waveform 200 to maintain at least substantially similar shapes, regardless of the charging status and discharging characteristics of the pulse generators 70, 72.

In addition, because the pulsatile biphasic waveform could be made not to cause stimulation of cardiac tissues, the impedance measuring circuit 112 may generate the pulse-train waveform 200 asynchronously, without having to synchronize the waveform 200 to the cardiac events such as the R-waves, the refractory periods of the cardiac tissues, or other similar events. However, if cardiac stimulation is unavoidable, the impedance measuring circuit 112 may generate the waveform 200 synchronously with the cardiac events.

The exponentially decreasing amplitudes of the pulses 210 of the pulse-train waveform 200 are primarily attributed to the nature of capacitive discharges, that is the output energies of the pulse generators 70, 72 are incrementally depleted while generating the successive pulses 210. This decrease allows for the estimation of the discharging time constant. From which, and by knowing the capacitance value of the generator, it is possible to calculate the patient lead impedance.

The impedance measuring circuit 112 may also regulate the durations of each pulse 210 of the pulse-train waveform 200 such that pre-selected amounts of electrical energy are delivered to the surrounding tissues through the leads 40, 56, 58 during each pulse 210 of the waveform 200.

The impedance measuring circuit 112 also causes a pulse 210 to be followed by a succeeding pulse with an opposite polarity. In general, approximately 3 volts of monophasic pulses are consumed through the polarization of the electrodes 40, 56 and 58, in particular between the polished surfaces of these electrodes and the surrounding body fluid such as blood. This undesirable voltage drop not only obscure the signals, but also compounds the inaccuracy in measuring the lead impedance.

The biphasic pulse-train waveform 200 of the present invention advantageously cancels the polarization voltage drops that would otherwise be present across the electrodes 40, 56 and 58 for two reasons. The biphasic pulse-train has a better charge balance (i.e., a net charge of approximately 0) and further has a higher frequency content than the monophasic waveform. Since the electrode/electrolyte interface has a capacitive components (helmholtz capacitor), the charge balance results in less voltage remaining on that capacitor. Also the higher frequency content of the waveform passes easier through this capacitor.

In addition, the alternating polarities of the biphasic pulse-train waveform 200 may further cancel or neutralize the stimulation of the nerves and/or excitable cardiac tissues. To this end, the impedance measuring circuit 112 preferably delivers the pulses 210 in alternating pairs or, in other words, deliver a pulse-train waveform 200 with the same number of positive and negative pulses 210. It being understood that each pulse 210 of the pulse-train waveform 200 may preferably be immediately followed by a succeeding pulse 210 with an opposite polarity, so that the tissue sees them as a single biphasic pulse.

The foregoing biphasic pulse-train waveforms 200 offers various benefits over conventional monophasic and monotonous waveforms. The pulsatility and alternating polarity of the biphasic pulse-train waveform 200 has a higher stimulation threshold of the motor or sensory nerves and excitable tissues. Thus, the impedance measuring circuit 112 of the present invention can employ pulse-train waveforms 200 with higher amplitudes, and can further improve the accuracy in measuring the lead impedance of the electrodes and/or leads.

In addition, the impedance measuring circuit 112 can deliver the pulse-train waveform 200 for a prolonged duration so that the terminal pulse 211 of the waveform 200 has a lower amplitude than the initial pulse 212, thereby generating a greater voltage drop between the initial pulse 212 and the terminal pulse 211. This also contributes to an improvement in the measurement accuracy. Furthermore, the alternating biphasic feature of the pulse-train waveform 200 as well as a much shorter duration of each pulse (i.e., higher frequency) avoid, or at least minimize the polarization between the surfaces of the electrodes and the surrounding body fluid.

FIG. 5 is a graph of another exemplary biphasic pulse-train waveform 215 that is formed of a sequence of two or more relatively short biphasic pulse-train waveforms, e.g., 220, 230. The pulse-train waveform 215 is used by the impedance measuring circuit 112 for impedance measurement according to an alternative embodiment of the present invention.

Each of the pulse-train waveforms 220, 230 has a generally similar shape to that of the waveform 200 of FIG. 4, but has a shorter duration so that it is not felt by the patient. The pulse-train waveforms 220, 230 are separated by an interval 235, that could be for example one cardiac cycle. One feature of this alternative embodiment is that the effective pulse delivery time, or effective on-time, is used for impedance measurement.

The alternative embodiment of FIG. 5 illustrates that the waveform 215 may be time-split into several groups of pulse-pairs. As an example, five pulse pairs may be delivered in a single train 220, followed by five more pairs that are similarly delivered in a single train 230, at a programmable delay or interval 235. Alternatively, the second train 230 may be synchronized to a specific cardiac event or to a sensed biological event. Several pulse trains may deliver a larger number of total pulses, such that the total energy discharge is spread over a longer effective on-time pulse delivery period. By increasing the total delivery energy, the accuracy of the impedance calculation can be improved.

For both exemplary biphasic waveforms 200 and 215 (FIGS. 4 and 5) the patient impedance "R" can be measured by the following expression:

$$R = \frac{d}{\left(\ln\left(\frac{Vleading}{Vtrailing}\right) \cdot C\right)},$$

where $V_{trailing}$ is the end or trailing voltage after pulse delivery; $V_{leading}$ is the starting or leading voltage of the biphasic waveforms 200 and 215, such as initial waveform 212 (FIG. 4), d is the effective on-time which is the effective duration of the pulses where the effective on-time is equal to the sum of all individual pulse durations; and C is the capacitance of the generator or ICD that is predetermined. The only variable in the above expression, is the impedance "R" that can be readily computed knowing the other values. The foregoing expression is calculated for the entire train.

FIG. 6 illustrates an ICD output switch configuration 300 comprised of a pulse generator 310 (such as the atrial and ventricular pulse generators 70, 72), a switch bank 320 (such as the electrical configuration switch 74), and a controller (such as the microcontroller 60). The pulse generator 310 receives power from the energy cells and generates the pulse-train waveforms 200 (or 220 and 230). The switch bank 320 is coupled to the pulse generator 310 and generally has a plurality of switches to connect or disconnect the pulse generator 310 to and from the electrodes 40, 56 and 58. More particularly, the switch bank 320 may include at least one H-shaped bridge (or "H-bridge") 100 (FIG. 7) in which at least two switches are implemented in each leg.

The microcontroller 60 controls the normal operation of the stimulation device 10, and further regulates the actuation (i.e., opening and closing of) the switches within the switch bank 330. More particularly, the microcontroller 60 is preferably provided with complete electrode programmability (e.g., switching operation and connection arrangements) so that it may regulate the timing for generating and/or terminating the pulse-train waveforms 200, 220, 230, the durations, frequencies and amplitudes of the pulses of these pulse-train waveforms 200, 220, 230, the intervals between the waveforms 200, 220, 230 when multiple waveforms are delivered to the electrodes 40, 56 and 58.

Thus, various aspects and embodiments of impedance measuring systems and methods thereof for the implantable cardiac stimulation devices have been described in which the pulse-train waveforms that has a higher stimulation threshold of various nerves and excitable tissues, thereby making it less perceptible by the patient while also enhancing the measurements accuracy. While detailed descriptions of the specific embodiments of this invention have been provided, it would be apparent to those skilled in the art that numerous variations of the systems and methods described herein may be possible in which the concepts of this invention may readily be applied. The descriptions provided herein are for the sake of illustration and in no aspect intended to be limiting.

What is claimed is:

1. In an implantable cardiac stimulation device, a method of measuring lead impedance comprising:
   generating a biphasic pulse train comprised of a first set of pulses of a first polarity and a second set of pulses of a second polarity that is opposite to the first polarity;
   delivering the biphasic pulse train through the lead in a preselected temporal relation that minimizes tissue stimulation and polarization between the tissue and the lead; and
   calculating a lead impedance as a function of an initial measured voltage and a post-delivery measured voltage.

2. The method of claim 1, wherein the first and second sets of pulses are grouped in a paired arrangement of alternating polarities.

3. The method of claim 2, wherein at least some of the first and second sets of pulses are of equal duration.

4. The method of claim 3, wherein the duration of the pulses ranges between approximately 10% and 15% of a time constant of stimulation of the tissue.

5. The method of claim 4, wherein the duration of each of the pulses is less than approximately 50 μsec.

6. The method of claim 5, wherein at least one pulse of the first and second sets of pulses has a voltage higher than 12 volts.

7. The method of claim 6, wherein the first set of pulses has a voltage that decreases exponentially over time.

8. The method of claim 7, wherein the second set of pulses has a voltage that decreases exponentially over time.

9. The method of claim 1, wherein generating the biphasic pulse train comprises generating a waveform that is formed of a sequence of two or more short biphasic pulse-trains.

10. The method of claim 9, wherein the sequence of two or more short biphasic pulse-trains comprises at least a first pulse train and a second pulse train; and
   wherein the first and second pulse trains are synchronized to cardiac events.

11. The method of claim 9, wherein the sequence of two or more short biphasic pulse-trains comprises at least a first pulse train and a second pulse train; and
   wherein the first and second pulse trains are synchronized to a predetermined sensed biological event.

12. The method of claim 1 wherein at least one pulse in the pulse train has an amplitude sufficient to cause tissue stimulation and the preselected temporal relation minimizes the tissue stimulation that would otherwise be caused by the at least one pulse.

13. A system for measuring lead impedance, for use with a stimulation device, comprising:

a pulse generator that generates a biphasic pulse train comprised of a first set of pulses of a first polarity and a second set of pulses of a second polarity that is opposite to the first polarity;

a lead that delivers the biphasic pulse train in a preselected temporal relation that minimizes tissue stimulation and polarization between the tissue and the lead; and an impedance measuring circuit that calculates a lead impedance as a function of an initial measured voltage and a post-delivery measured voltage.

14. The system of claim 13, wherein the first and second sets of pulses are grouped in a paired arrangement of alternating polarities.

15. The system of claim 13, wherein at least some of the first and second sets of pulses are of equal duration.

16. The system of claim 15, wherein the duration of the pulses ranges between approximately 10% and 15% of a time constant of stimulation of the tissue.

17. The system of claim 16, wherein the duration of each of the pulses is less than approximately 50 μsec.

18. The system of claim 15, wherein at least one pulse of the first and second sets of pulses has a voltage higher than 12 volts.

19. The system of claim 13, wherein the biphasic pulse train comprises a waveform that is formed of a sequence of two or more short biphasic pulse-trains.

20. The system of claim 19, wherein the sequence of two or more short biphasic pulse-trains comprises at least a first pulse train and a second pulse train; and wherein the first and second pulse trains are synchronized to cardiac events.

21. The system of claim 19, wherein the sequence of two or more short biphasic pulse-trains comprises at least a first pulse train and a second pulse train; and wherein the first and second pulse trains are synchronized to a predetermined sensed biological event.

22. The system of claim 13 wherein at least one pulse in the pulse train has an amplitude sufficient to cause tissue stimulation and the preselected temporal relation minimizes the tissue stimulation that would otherwise be caused by the at least one pulse.

23. A system for measuring lead impedance, for use with a stimulation device, the system comprising:

means for generating a pulse train comprising a first set of pulses of a first polarity and a second set of pulses of a second polarity that is opposite to the first polarity, the pulse train formed of a sequence of two or more short biphasic pulse-trains;

means for delivering the pulse train in a way that minimizes tissue stimulation and polarization between the tissue and the lead; and means for calculating a lead impedance.

24. The system of claim 23, wherein each of the short biphasic pulse-trains contains a series of consecutive pulses of opposite polarities.

25. The system of claim 24, wherein each of the pulses in the series of consecutive pulses has a duration and an amplitude set to avoid a generation of stimulation sensation.

* * * * *